(12) United States Patent
Siems et al.

(10) Patent No.: US 10,653,172 B2
(45) Date of Patent: May 19, 2020

(54) NATURAL STILBENES AS SWEETENERS OR SWEETENER ENHANCER

(71) Applicant: Analyticon Discovery GmbH, Potsdam (DE)

(72) Inventors: Karsten Siems, Michendorf (DE); Grit Kluge, Trebbin (DE); Sven Jakupovic, Berlin (DE); Fotini Tsichrintzi, Berlin (DE); Gregor Hetterling, Berlin (DE)

(73) Assignee: Analyticon Discovery GmbH, Potsdam (DE)

( * ) Notice: Subject to any disclaimer, the term of this patent is extended or adjusted under 35 U.S.C. 154(b) by 0 days.

(21) Appl. No.: 15/740,208

(22) PCT Filed: Jun. 25, 2016

(86) PCT No.: PCT/EP2016/064767
§ 371 (c)(1),
(2) Date: Dec. 27, 2017

(87) PCT Pub. No.: WO2017/005515
PCT Pub. Date: Jan. 12, 2017

(65) Prior Publication Data
US 2018/0168210 A1 Jun. 21, 2018

(30) Foreign Application Priority Data
Jul. 3, 2015 (EP) ..................... 15175181

(51) Int. Cl.
| | | |
|---|---|---|
| *A61K 36/00* | (2006.01) | |
| *A23L 27/30* | (2016.01) | |
| *A23L 27/00* | (2016.01) | |
| *A61K 8/60* | (2006.01) | |
| *A61K 47/26* | (2006.01) | |
| *A61Q 11/00* | (2006.01) | |
| *B01D 15/32* | (2006.01) | |

(52) U.S. Cl.
CPC .............. *A23L 27/33* (2016.08); *A23L 27/30* (2016.08); *A23L 27/88* (2016.08); *A61K 8/602* (2013.01); *A61K 47/26* (2013.01); *A61Q 11/00* (2013.01); *A23V 2002/00* (2013.01); *B01D 15/325* (2013.01)

(58) Field of Classification Search
None
See application file for complete search history.

(56) References Cited

U.S. PATENT DOCUMENTS

| | | | |
|---|---|---|---|
| 2007/0116838 A1 | 5/2007 | Prakash et al. | |
| 2008/0268097 A1* | 10/2008 | Hurst | ..................... A23G 1/002 426/45 |

FOREIGN PATENT DOCUMENTS

| | | |
|---|---|---|
| CN | 101669995 A | 3/2010 |
| CN | 104489646 A | 4/2015 |

OTHER PUBLICATIONS

Lin et al. (1992) Phytochemistry, vol. 31, No. 2, pp. 633-638. (Year: 1992).*
Xu et al. (1997) Chinese Chemical Letters, vol. 8, No. 6, pp. 509-510. (Year: 1997).*
Iliya et al. (2003) Phytochemistry 62: 601-606. (Year: 2003).*
Zaman et al. (1983) Indian Journal of Chemistry, vol. 22B, pp. 101-104. (Year: 1983).*
Kato et al. (2009) J. Agric. Food Chem. 57, pp. 2544-2549. (Year: 2009).*
Yao et al. (2012) Journal of Asian Natural Products Research, vol. 14, No. 9, 918-922. (Year: 2012).*
Vastano et al., "Isolation and Identification of Stilbenes in Two Varieties of Polygonum cuspidatum," J. Agric. Food Chem. (2000) 48: 253-256.
Wang et al., "Stilbene Derivatives from Gnetum montanum MARKGR. f. megalocarpum MARKGR.," Helvetica Chimica Acta (2008) 91: 159-164.
Iliya et al., "Five Stilbene Glucosides from Gnetum gnemonoides and Gnetum africanum," Helvetica Chimica Acta (2002) 85: 2394-2402.

* cited by examiner

Primary Examiner — Terry A McKelvey
Assistant Examiner — Russell G Fiebig
(74) Attorney, Agent, or Firm — Dilworth & Barrese, LLP

(57) ABSTRACT

Suggested are compositions comprising natural stilbenes as a sweetener or sweetener enhancer in preparations and compositions, especially oral edible compositions comprising them.

14 Claims, 4 Drawing Sheets

NATURAL STILBENES AS SWEETENERS OR SWEETENER ENHANCER

FIELD OF INVENTION

The invention relates to stilbenoids, which are obtainable by the extraction from different plant species and its physiologically acceptable salts which are useful as a sweetener or sweetener enhancer in preparations and compositions, especially oral edible compositions.

STATE OF THE ART

Sweetness is one of the primary taste and cravings of both animals and humans. The universal use of naturally occurring and synthetic sweeteners to satisfy this natural craving has not been met without its accompanying physiological disadvantages, e.g. obesity, nutritional imbalance and dental decay. To overcome these unwanted disadvantages considerable research efforts and expenditures have been made to develop alternative compounds, e.g. as substitute for the naturally occurring sweeteners or synthetic sweeteners which have no food value and are free of caloric input. While these artificial sweeteners enjoyed a wide use, and fulfilled the requirements of a sweet taste with no food value, and could be used without providing calories or damaging teeth, they were frequently found to possess inherent disadvantages that prevented their use for their intended purpose, e.g. because of their toxicity (p-ethoxyphenylurea) or chromosome damage and bladder trouble (sodium cyclamate). Thus, these sweeteners could not be safely recommended for use as a sweetener and are apparently unacceptable for consumption. Saccharin compounds are also commonly used as artificial sweeteners, since cyclamates have been come under governmental restrictions. Although saccharin compounds possess sweetness characteristics, they are undesirable as the sole sweetening agent in most food and beverage compositions because of the lingering bitter aftertaste perceived by most users. While saccharin and the cyclamates have been in common use as artificial sweetening agents for a number of years, there has been more recently discovered a series of new artificial sweeteners.

For example, Horowitz and Gentili, U.S. Pat. No. 3,087,821, teach the use of various dihydrochalcones having sugar substituents (dihydrochalcones glycosides) as sweetening agents. All sweet dihydrochalkones have a licorice like aftertaste and linger in the mouth for some time.

*Siraitia grosvenori* (Luo han guo), a member of the Cucurbitaceae family, is a plant native to some regions of southern Asia and China. The sweet taste of fruits of luo han guo mainly comes from triterpene glycosides generally known as mogrosides. There are a number of mogrosides identified in luo han guo but generally mogroside V (CAS No: 88901-36-4) has the highest concentration compared to others (Table 1). Mogrol glycosides have the same core molecule—mogrol or oxo-mogrol and differ from each other by number and type of glycosidic residues bonded to mogrol or oxo-mogrol molecules (US 2012/0059071, Kasai et al. Agric. Biol. Chem. (1989), 3347-3349), Matsumoto et. al. Chem. Pharm. Bu. (1990) 2030-2032. Several mogrosides taste very sweet, often >100× sweeter than sucrose, including the major triterpen glycoside of *Siraitia grosvenori*, mogroside V, and its isomer iso-mogroside V (US2011/0027413), but all of them have a certain bitter aftertaste.

Leaves of *Stevia rebaudiana* are well known for its sweet taste due to its content of sweet diterpene glycosides. One of the major sweet compounds from *stevia*, Rebaudioside A, is approved as natural sweetener in US (since 2008) and EU (since 2011). Apart from its sweet taste, all sweeteners from *stevia* have a slower onset and longer duration than that of sugar, and a bitter or licorice-like aftertaste at high concentrations (Lemus-Mondaca et al. Food Chemistry 132 (2012) 1121-1132).

Accordingly, it is a primary object of the present invention to provide novel sweetener compounds and its physiologically acceptable salts, which have a positive sweet benefit in food and oral compositions. In particular, the object was to provide sweetener compounds which are capable to provide sweetness to consumable compositions in a way, that the balance between the degree of sweetness and the amount which has to be administered to obtain a sweet effect is comparable low, to overcome the aforesaid disadvantages associated with the prior art sweetener. It is another object of the present invention to provide sweetener compounds without astringent or bitter-taste aftertaste. The sweetener compounds to be specified should be toxicologically safe, effective already at relatively low concentrations, well tolerated by the digestion, stable (in particular in normal cosmetic and/or pharmaceutical formulations), and easy to formulate and economical to produce.

DESCRIPTION OF THE INVENTION

Object of the present invention is a sweetener composition comprising at least one compound of general formula (I)

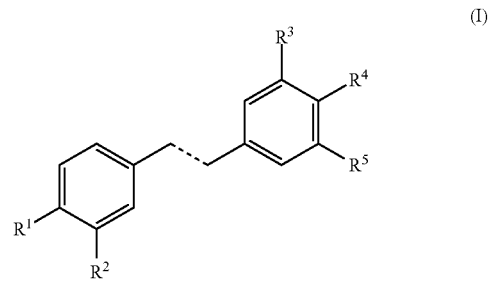

wherein $R^1$ to $R^5$ are independently of one another and denote hydrogen, hydroxyl, methoxy or a sugar moiety, said sugar moiety being selected from the group consisting of a monosaccharide and/or oligosaccharide.

Preferably in the sweetener compound of formula (I) the monosaccharide is selected from the group consisting of fructose, glucose, mannose, rhamnose, galactose, glucuronic acid, quinovose, fucose, arabinopyranose, arabinofuranose, xylopyranose, xylofuranose or apiose (2,3,4-trihydroxy-3-(hydroxymethyl)butanal).

In the course of extensive studies on sweeteners, the present inventors succeeded in the isolation of novel sweetener compounds of formula (I) and found that these sweetener compounds of formula (I) show astonishingly good and strong sweetness when compared with that of sucrose and known natural high intensity sweeteners like rebaudiosides and mogrosides.

Surprisingly, it has been further observed that the sweetener compounds of formula (I) have significantly less negative aftertaste at all and have high sweetening power.

BRIEF DESCRIPTION OF THE DRAWINGS

The present invention will be described in greater detail with reference to the accompanying drawings in which FIGS. 1-4 respectively illustrate the NMR spectroscopy and mass spectroscopy of preferred compounds according to the present invention.

PREFERRED COMPOUNDS

Figure 1:
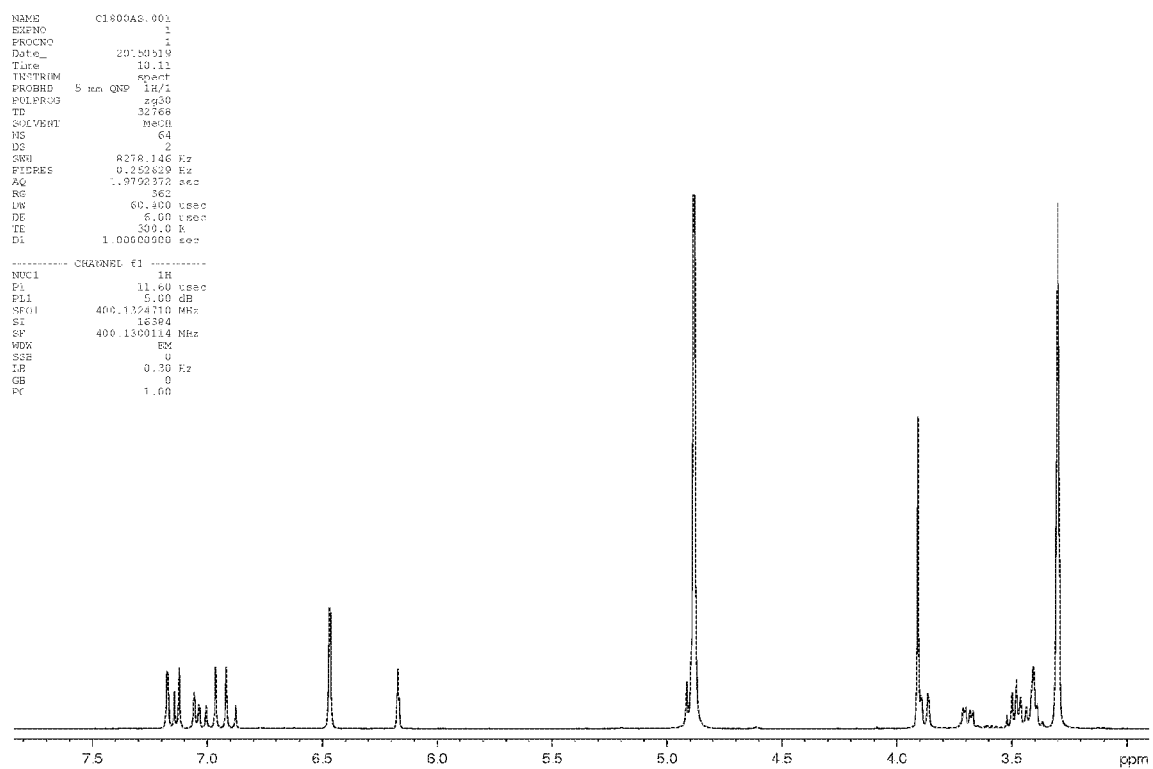
Figure 2:
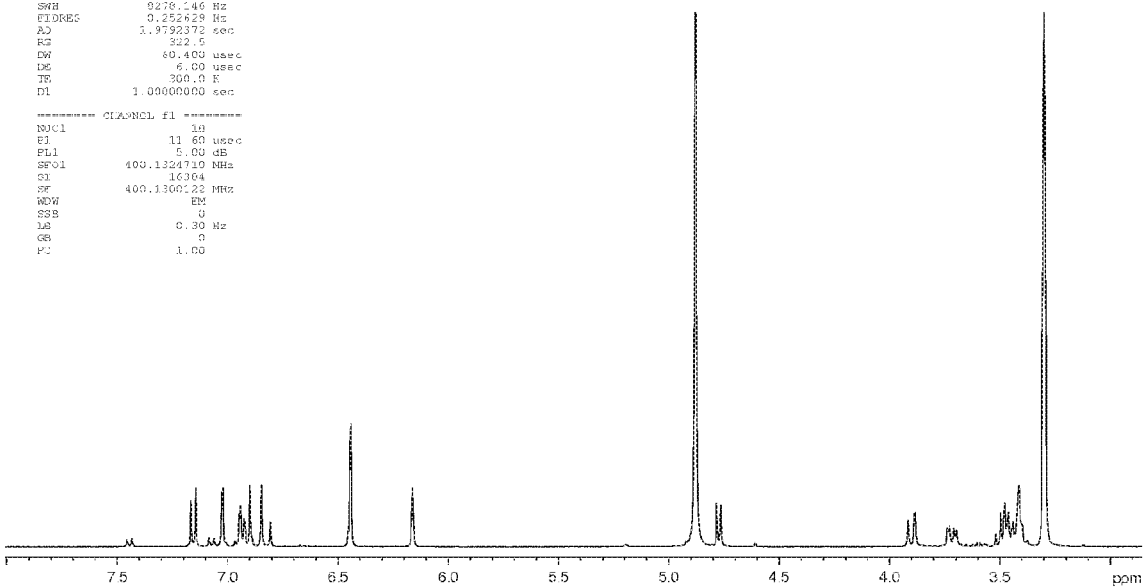
Figure 3:
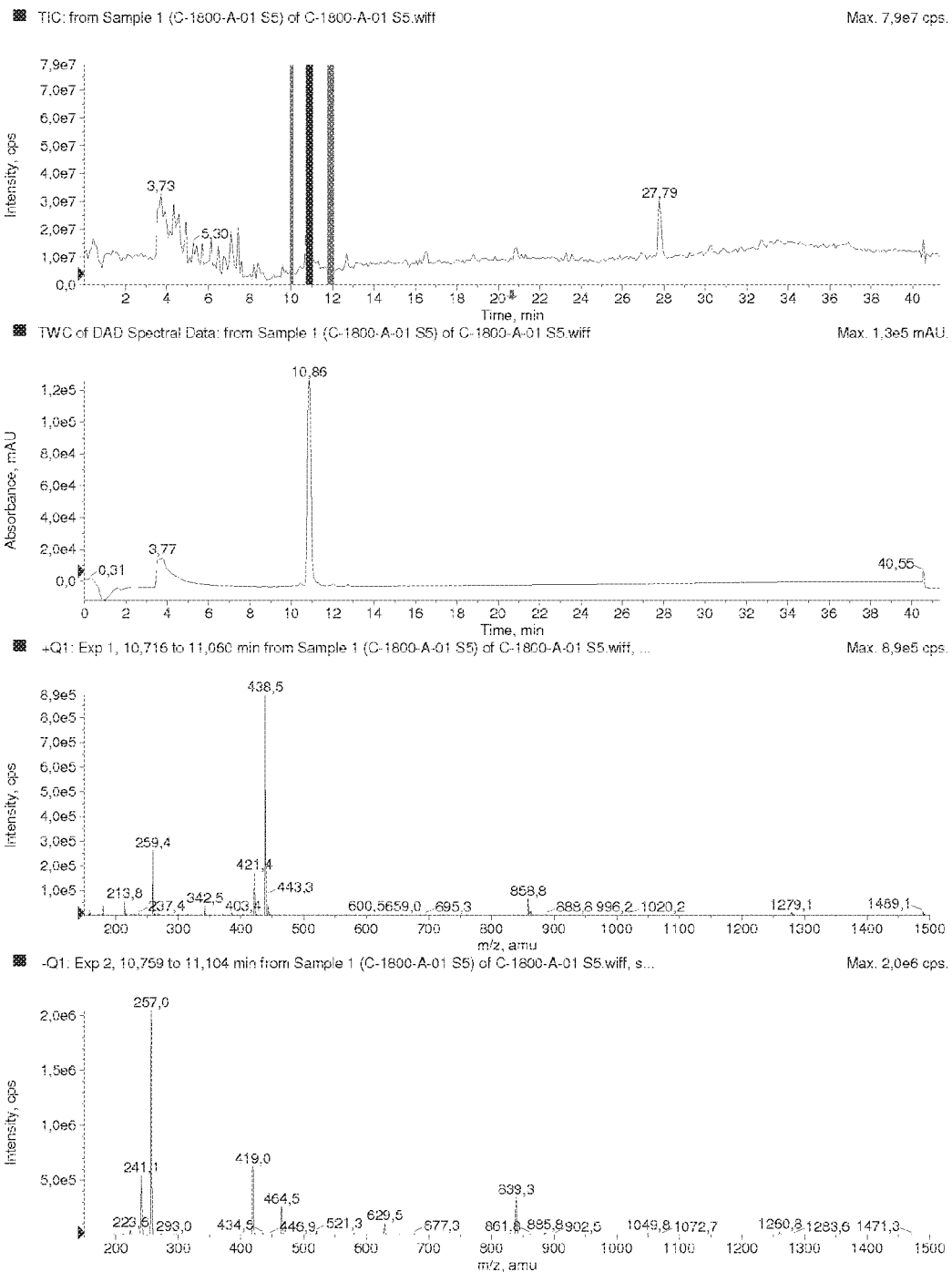
Figure 4:
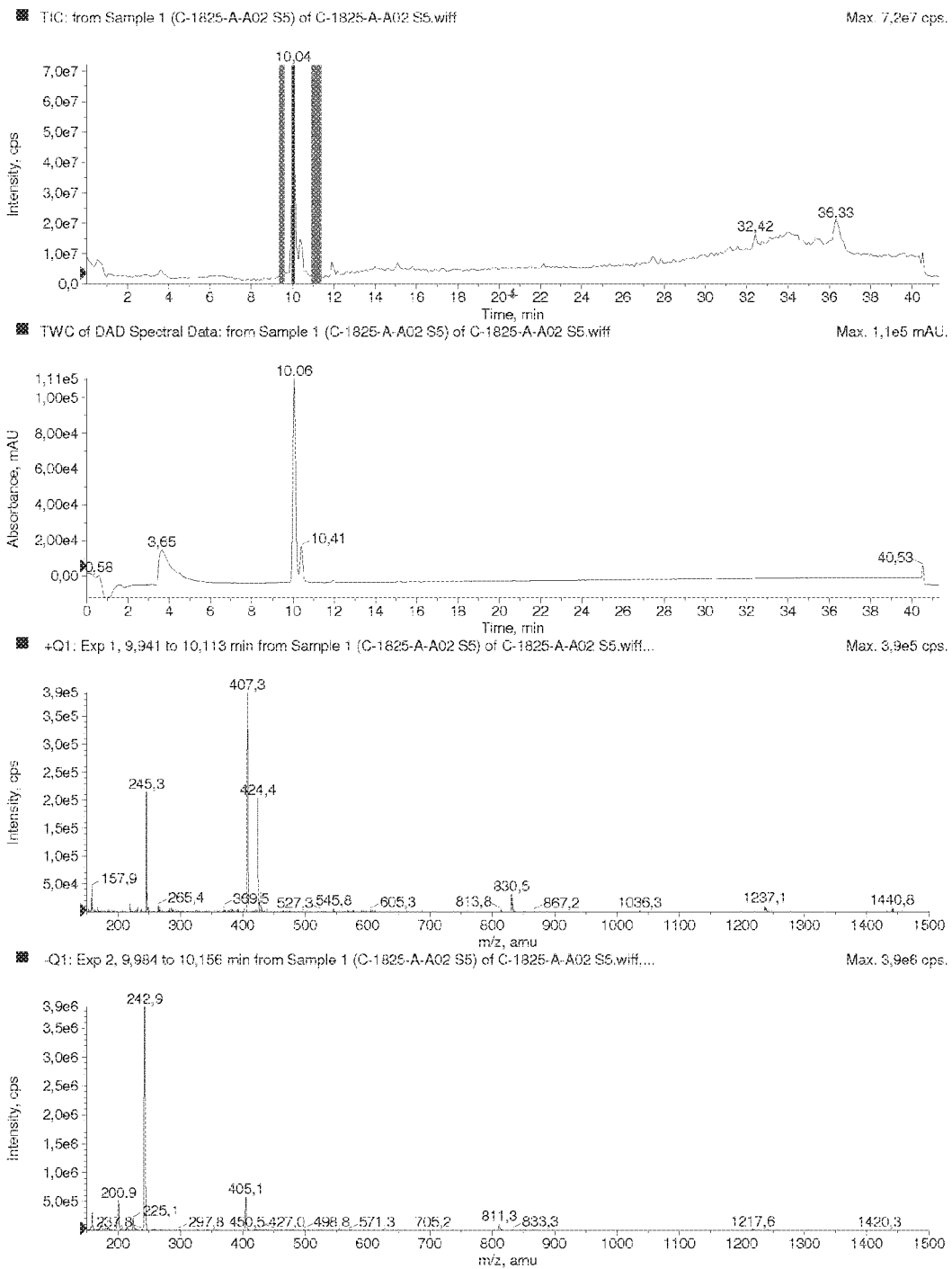

Of particular interest are the compounds of Formula (I) identified as:
Compound A
Gnetifolin E

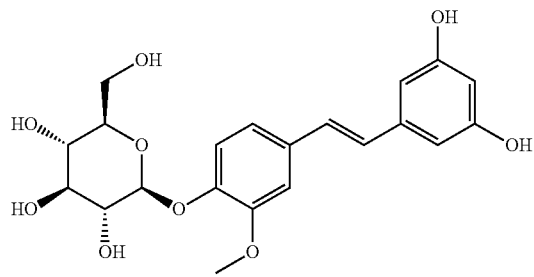 [SMILES: COc1cc(/C=C/c2cc(O)cc(O)c2)ccc1O[C@@H]1O[C@H](CO)[C@@H](O)[C@H](O)[C@H]1O]

Compound B
Piceatannol 4'-O-β-D-glucopyranoside

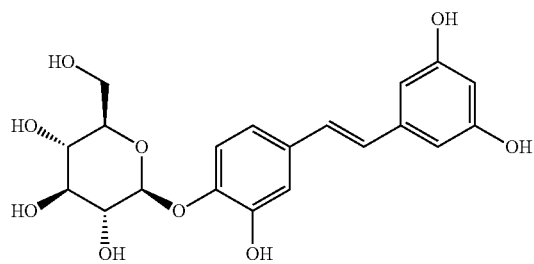 [SMILES: OC[C@H]1O[C@@H](Oc2ccc(/C=C/c3cc(O)cc(O)c3)cc2O)[C@H](O)[C@@H](O)[C@@H]1O]

Extracts and Extraction Process

Another object of the present invention refers to an extract comprising one or more of a compound of formula (I) obtainable by aqueous and/or alcoholic extraction of at least one plant selected from the group consisting of *Gnetum, Picea, Rheum, Eucalyptus, Bauhinia* and *Polygonum*. Preferably said plants are selected from the group consisting of:
  *Gnetum formosum*
  *Gnetum montanum*
  *Picea abies*
  *Picea glauca*
  *Rheum officinale*
  *Rheum palmatum*
  *Rheum rhaponticum*
  *Rheum emodi*
  *Rheum rhbarbarum*
  *Eucalyptus globulus*
  *Eucalyptus camaldudensis*
  *Bauhinia cardinalis*
  *Polygonum sacchalinense*
  *Polygonum japonicum*

More preferably said extracts are rich in at least one compound of formula (I) selected from the group consisting of Gnetifolin E and Piceatannol-4'-O-ß-D-glucoside.

The extracts according to the present invention may be prepared by methods known per se, i.e. for example by aqueous, alcoholic or aqueous/alcoholic extraction of the plants or parts thereof. Suitable extraction processes are any conventional extraction processes, such as maceration, re-maceration, digestion, agitation maceration, vortex extraction, ultrasonic extraction, counter current extraction, percolation, re-percolation, evacolation (extraction under reduced pressure), diacolation and solid/liquid extraction under continuous reflux. Percolation is advantageous for industrial use.

The plant materials that are useful for obtaining the abstracts may include parts of the whole plant selected from the group consisting of blossoms, fruits, buds, roots, seeds and/or leaves or the whole plant itself. Leaves, stems or roots, however, are preferably used as the starting material and may be mechanically size-reduced before the extraction process. Any size reduction methods known to the expert, for example freeze grinding, may be used. Preferred solvents for the extraction process are organic solvents, water (preferably hot water with a temperature above 80° C. and more particularly above 95° C. or mixtures of organic solvents and water, more particularly low molecular weight alcohols with more or less high water contents. Extraction with methanol, ethanol and water-containing mixtures thereof is particularly preferred. The extraction process is generally carried out at about 20 to about 100° C. and preferably at about 50 to about 70° C. In one preferred embodiment, the extraction process is carried out in an inert gas atmosphere to avoid oxidation of the ingredients of the extract. This is particularly important where extraction is carried out at temperatures above 40° C. The extraction times are selected by the expert in dependence upon the starting material, the extraction process, the extraction temperature and the ratio of solvent to raw material, etc. After the extraction process, the crude extracts obtained may optionally be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of the starting materials are of the order of about 1 to about 20, %, preferably about 2 to about and more preferably about 5 to about 10% b.w.—calculated on the starting materials. Particular preferred is a process for obtaining an extract rich in compounds according to formula (I) encompassing the steps of:
  (a) Providing a suspension of leaves of *Gnetum, Picea, Rheum, Eucalyptus, Bauhinia* or *Polygonum*, or mixtures thereof in water, a $C_1$-$C_4$ aliphatic alcohol or their mixtures,
  (b) Subjecting said suspension to extraction using water, a $C_1$-$C_4$ aliphatic alcohol or their mixtures at temperatures of about 20° C. to about 80° C., and optionally
  (c) Separating off the solvent.

It should be noted that the content in the extract of each of the compounds (A) and (B) differs from batch to batch depending on the used raw material of leaves or roots of the plants cited above.

Compositions

The preparation of the present invention comprising at least one sweetener compound of formula (I) and can be used to impart a desirable sweetness and/or flavor to a variety of oral and food compositions and pharmaceutical compositions, such as beverages, edible foodstuff, dentifrices, lipsticks and the like, which may or may not be ingestible, with or without the use of other flavorants and sweeteners. The present invention also relates to a variety of oral and food compositions and the like embodying at least one compound of formula (I) as sweetener and/or flavoring agent.

The sweetener of this invention finds application in the wide range of edible substances generally, primarily in food compositions such as candies, confections and processed foods, and beverages such as beer and soft drinks. It is also well suited for imparting a sweet flavor to other edible substances such as medicines, toothpaste, adhesives for stamps and envelopes, animal feeds and baits and the like. These examples are given solely for illustration and it is not wished to limit the scope of this invention to sweetening any particular type or types of edible materials. As a general rule, the present sweetener may be used in any application where a sweet taste is desired. The present sweetener may be used alone or in combination with other sweeteners, nutritive or nonnutritive. Also, if desired, binders or diluents may be added to the sweetener. This is not usually necessary, however, as the sweetener is a solid having excellent handling properties. This makes mixing the sweetener with an edible substance a simple conventional operation. The sweetener may be mixed with the edible substance as a solid or as a solution, if desired.

The inventions further refers to the use of a sweetener compound of formula (I) to sweet or enhance the sweeting effect in compositions or preparations which are administered to an individual in an effective amount sufficient to produce the desired degree of sweetness.

Thus the invention further relates to a method for providing a sweetening effect and/or an enhanced sweetening effect in compositions, comprising administering to an individual a sweetener compound of formula (I) in an effective amount sufficient to produce the desired degree of sweetness.

The effective amount is preferably from 1 ppm to 2000 ppm, based on the total weight of the composition and the total sum of all compound of formula (I).

The food, oral and pharmaceutical compositions will be further described in detail.

Food Compositions

Another object of the present invention refers to a food composition, comprising the sweetener composition or the extract as disclosed above.

Food compositions according to the invention are any preparations or compositions which are suitable for consumption and are used for nutrition or enjoyment purposes, and are generally products which are intended to be introduced into the human or animal oral cavity, to remain there for a certain time and then either be eaten (e.g. ready-to-eat foodstuffs or feeds, see also herein below) or removed from the oral cavity again (e.g. chewing gums). Such products include any substances or products which in the processed, partially processed or unprocessed state are to be ingested by humans or animals. They also include substances which are added to orally consumable products during their manufacture, preparation or treatment and which are intended to be introduced into the human or animal oral cavity.

The food compositions according to the invention also include substances which in the unchanged, treated or prepared state are to be swallowed by a human or animal and then digested; in this respect, the orally consumable products according to the invention also include casings, coatings or other encapsulations which are to be swallowed at the same time or which may be expected to be swallowed. The expression "orally consumable product" covers ready-to-eat foodstuffs and feeds, that is to say foodstuffs or feeds that are already complete in terms of the substances that are important for the taste. The expressions "ready-to-eat foodstuff" and "ready-to-eat feed" also include drinks as well as solid or semi-solid ready-to-eat foodstuffs or feeds. Examples which may be mentioned are frozen products, which must be thawed and heated to eating temperature before they are eaten. Products such as yoghurt or ice-cream as well as chewing gums or hard caramels are also included among the ready-to-eat foodstuffs or feeds.

Preferred food compositions according to the invention also include "semi-finished products". Within the context of the present text, a semi-finished product is to be understood as being an orally consumable product which, because of a very high content of flavourings and taste-imparting substances, is unsuitable for use as a ready-to-eat orally consumable product (in particular foodstuff or feed). Only by mixing with at least one further constituent (e.g. by reducing the concentration of the flavourings and taste-imparting substances in question) and optionally further process steps (e.g. heating, freezing) is the semi-finished product converted into a ready-to-eat orally consumable product (in particular foodstuff or feed). Examples of semi-finished products which may be mentioned here are Food composition according to the invention preferably comprises one or more preparations for nutrition or enjoyment purposes. These include in particular (reduced-calorie) baked goods (e.g. bread, dry biscuits, cakes, other baked articles), confectionery (e.g. chocolates, chocolate bars, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshing drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, precooked ready-to-eat rice products), dairy products (e.g. full-fat or reduced-fat or fat-free milk drinks, rice pudding, yoghurt, kefir, cream cheese, soft cheese, hard cheese, dried milk powder, whey, butter, buttermilk, partially or completely hydrolysed milk-protein-containing products), products made from soy protein or other soybean fractions (e.g. soy milk and products produced therefrom, drinks containing isolated or enzymatically treated soy protein, drinks containing soy flour, preparations containing soy lecithin, fermented products such as tofu or tempeh or products produced therefrom and mixtures with fruit preparations and optionally flavours), fruit preparations (e.g. jams, sorbets, fruit sauces, fruit fillings), vegetable preparations (e.g. ketchup, sauces, dried vegetables, frozen vegetables, precooked vegetables, boiled-down vegetables), snacks (e.g. baked or fried potato crisps or potato dough products, maize- or groundnut-based extrudates), fat- and oil-based products or emulsions thereof (e.g. mayonnaise, remoulade, dressings, in each case full-fat or reduced-fat), other ready-made dishes and soups (e.g. dried soups, instant soups, precooked soups), spices, spice mixtures and in particular seasonings which are used, for example, in the snacks field, sweetener preparations, tablets or sachets, other preparations for sweetening or whitening drinks or other foods. The preparations within the scope of the invention can also be used in the form of semi-finished products for the production of further preparations for nutrition or enjoyment purposes. The preparations within the scope of the invention can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, and in the form of food supplements.

The preparations can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, for example in the form of food supplements.

The semi-finished products are generally used for the production of ready-to-use or ready-to-eat preparations for nutrition or enjoyment purposes.

Further constituents of a ready-to-eat preparation or semi-finished product for nutrition or enjoyment purposes can be conventional base substances, auxiliary substances and additives for foods or enjoyment foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices, vegetable pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, cocoa fat, hardened vegetable fat), oils (e.g. sunflower oil, groundnut oil, maize germ oil, olive oil, fish oil, soya oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste correctors for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilisers (e.g. carrageenan, alginate), preservatives (e.g. benzoic acid and its salts, sorbic acid and its salts), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonene, amarogentine, humulone, lupulone, catechols, tannins), substances that prevent enzymatic browning (e.g. sulfite, ascorbic acid), ethereal oils, plant extracts, natural or synthetic colourings or colouring pigments (e.g. carotinoids, flavonoids, anthocyans, chlorophyll and derivatives thereof), spices, trigeminally active substances or plant extracts containing such trigeminally active substances, synthetic, natural or nature-identical flavourings or odorants as well as odour correctors.

Food compositions according to the invention, for example those in the form of preparations or semi-finished products, preferably comprise a flavour composition in order to complete and refine the taste and/or odour. A preparation can comprise as constituents a solid carrier and a flavour composition. Suitable flavour compositions comprise, for example, synthetic, natural or nature-identical flavourings, odorants and taste-imparting substances, reaction flavourings, smoke flavourings or other flavour-giving preparations (e.g. protein (partial) hydrolysates, preferably protein (partial) hydrolysates having a high arginine content, barbecue flavourings, plant extracts, spices, spice preparations, vegetables and/or vegetable preparations) as well as suitable auxiliary substances and carriers. Particularly suitable here are the flavour compositions or constituents thereof which produce a roasted, meaty (in particular chicken, fish, seafood, beef, pork, lamb, mutton, goat), vegetable-like (in particular tomato, onion, garlic, celery, leek, mushroom, aubergine, seaweed), spicy (in particular black and white pepper, cardamom, nutmeg, pimento, mustard and mustard products), fried, yeast-like, boiled, fatty, salty and/or pungent flavour impression and accordingly can enhance the spicy impression. The flavour compositions generally comprise more than one of the mentioned ingredients.

The food compositions of the present invention are preferably selected from the group comprising
confectionery, preferably reduced-calorie or calorie-free confectionery, preferably selected from the group comprising muesli bar products, fruit gums, dragées, hard caramels and chewing gum,
non-alcoholic drinks, preferably selected from the group comprising green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit and vegetable juice preparations,
instant drinks, preferably selected from the group comprising instant (green, black, rooibos, herbal) tea drinks,
cereal products, preferably selected from the group comprising low-sugar and sugar-free breakfast cereals and muesli bars,
dairy products, preferably selected from the group comprising reduced-fat and fat-free milk drinks, yoghurt, kefir, whey, buttermilk and ice-cream,
products made from soy protein or other soybean fractions, preferably selected from the group comprising soy milk, products produced from soy milk, drinks containing isolated or enzymatically treated soy protein, drinks containing soy flour, preparations containing soy lecithin, products produced from preparations containing soy lecithin and mixtures with fruit preparations and optionally flavours,
sweetener preparations, tablets and sachets,
sugar-free dragées,
ice-cream, with or without milk-based constituents, preferably sugar-free.

Food Additives

The food compositions according to the present invention may further comprise components selected from the group consisting of additional sweeteners or sweet-tasting compounds, aroma compounds, flavouring compounds and their mixtures.

Aroma or Flavouring Compounds

Aroma compounds and flavouring agents are well known in the art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as *eucalyptus*, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, *eucalyptus* oil, thyme oil, cinnamon oil, clove oil, spruce needle oil, fennel oil, sage oil, aniseed oil, star anise oil, chamomile oil, and caraway oil, and their mixtures.

Sweeteners and Sweet-Tasting Substances

The term "sweeteners" here denotes substances having a relative sweetening power of at least 25, based on the sweetening power of sucrose (which accordingly has a sweetening power of 1). Sweeteners to be used in an orally consumable product (in particular foodstuff, feed or medicament) according to the invention (a) are preferably non-cariogenic and/or have an energy content of not more than 5 kcal per gram of the orally consumable product.

Advantageous sweeteners in a preferred orally consumable product (in particular foodstuff, feed or medicament) according to the invention are selected from the following groups (a1) and (a2):

Naturally occurring sweeteners, preferably selected from the group comprising
  miraculin, monellin, mabinlin, thaumatin, curculin, brazzein, pentaidin, D-phenylalanine, D-tryptophan, and extracts or fractions obtained from natural sources, comprising those amino acids and/or proteins, and the physiologically acceptable salts of those amino acids and/or proteins, in particular the sodium, potassium, calcium or ammonium salts;
neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, osladin, polypodoside A, strogin 1, strogin 2, strogin 4, selligueain A, dihydroquercetin 3-acetate, perillartin, telosmoside $A_{15}$, periandrin I-V, pterocaryosides, cyclocaryosides, mukuroziocides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizine, and the physiologically acceptable salts of those compounds, in particular the sodium, potassium, calcium or ammonium salts;
extracts or concentrated fractions of the extracts, selected from the group comprising *Thaumatococcus* extracts (katamfe plant), extracts from *Stevia* ssp. (in particular *Stevia rebaudiana*), swingle extracts (*Momordica* or *Siratia grosvenorii*, Luo-Han-Guo), extracts from *Glycyrrhiza* ssp. (in particular *Glycyrrhiza glabra*), extracts from *Rubus* ssp. (in particular *Rubus suavissimus*), and extracts from *Lippia dulcis*;

Synthetic sweet-tasting substances, preferably selected from the group comprising magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

Suitable sweet-tasting substances, including natural sources of these substances such as for example
  sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or
  vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice),
synthetic/enzymatic hydrolysates of starch or sucrose (e.g. invert sugar syrup, highly enriched fructose syrups made from corn starch),
fruit concentrates (e.g. from apples or pears, apple syrup, pear syrup),
sugar alcohols (e.g. erythritol, threitol, arabitol, ribitol, xylitol, sorbitol, mannitol, dulcitol, lactitol),
proteins (e.g. miraculin, monellin, thaumatin, curculin, brazzein), artificial sweeteners (magap, sodiumcyclamate, acesulfame K, neohesperidin dihydrochalcone, saccharin sodium salt, Aspartame®, superaspartame, neotame, alitame, sucralose, lugduname, carrelame, sucrononate, sucrooctate, monatin), certain sweet-tasting amino acids (glycine, D-leucine, D-threonine, D-asparagine, D-phenylalanine, D-tryptophan, L-proline), other sweet-tasting low-molecular substances, e.g. rebaudioside, steviosid, mogrosides, hernandulcin, phyllodulcin, dihydrochalcone glycosides, glycyrrhizin, glycyrrhetinic acid ammonium salt or other glycyrrhetinic acid derivatives, extracts from sweet tasting plants, in particular *Momordica grosvenori* [Luo Han Guo] *Hydrangea macrophylla*, *Stevia* ssp. (e.g. *Stevia rebaudiana*), *Rubus suavissimus*, *Polypodium vulgare*, *Abrus precatorius*, *Pterocarya paliurus*, *Baccharis gaudichaudiana*, *Albizia myriophylla*, *Bryonia dioica*, *Phlomis betonicoides*, *Hemsleya carnosiflora*, *Lippia dulcis*, *Gynostemma pentaphyllum*, *Glycyrrhiza glabra* (liquorice) or individual sweet tasting substances isolated from those plants.

Thickeners

Advantageous thickeners in a preferred orally consumable product (in particular foodstuff, feed or medicament) according to the invention are selected from the group comprising: crosslinked polyacrylic acids and derivatives thereof, polysaccharides and derivatives thereof, such as xanthan gum, agar-agar, alginates or tyloses, cellulose derivatives, for example carboxymethylcellulose or hydroxycarboxymethylcellulose, fatty alcohols, monoglycerides and fatty acids, polyvinyl alcohol and polyvinylpyrrolidone.

Preference is given according to the invention to an orally consumable product (in particular foodstuff or feed) which comprises milk thickened with lactic acid bacteria and/or cream thickened with lactic acid bacteria and which preferably is selected from the group comprising yoghurt, kefir and quark.

A food composition according to the invention comprising milk thickened with lactic acid bacteria and/or cream thickened with lactic acid bacteria is advantageously an orally consumable product which comprises a probiotic, wherein the probiotic is preferably selected from the group comprising *Bifidobacterium animalis* subsp. *lactis* BB-12, *Bifidobacterium animalis* subsp. *lactis* DN-173 010, *Bifidobacterium animalis* subsp. *lactis* HN019, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

Additives for Chewing Gums

Particular preference is given to an orally consumable product (in particular foodstuff, feed or medicament) according to the invention that is a chewing gum and comprises a chewing-gum base. The chewing-gum base is preferably selected from the group comprising chewing-gum or bubble-gum bases. The latter are softer, so that gum bubbles can also be formed therewith. Preferred chewing-gum bases according to the invention include, in addition to the natural resins or the natural latex chicle that are traditionally used, elastomers such as polyvinyl acetate (PVA), polyethylene, (low or medium molecular weight) polyisobutene (PIB), polybutadiene, isobutene-isoprene copolymers (butyl rubber), polyvinylethyl ether (PVE), polyvinylbutyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or U.S. Pat. No. 6,986,709. In addition, chewing-gum bases that are preferably to be used according to the invention preferably comprise further constituents such as, for example, (mineral) fillers, plasticisers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminium oxide, dicalcium phosphate, tricalcium phosphate, magnesium hydroxide and mixtures thereof. Suitable plasticisers, or agents for preventing adhesion (detackifiers), are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides such as lecithin, mono- and di-glycerides of fatty acids, for example glycerol monostearate.

Chewing gums according to the invention (in particular as disclosed above) preferably comprise constituents such as sugars of different types, sugar substitutes, other sweet-tasting substances, sugar alcohols (in particular sorbitol, xylitol, mannitol), ingredients having a cooling effect, taste correctors for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilisers, odour correctors and flavours (e.g. *eucalyptus*-menthol, cherry, strawberry, grapefruit, vanilla, banana, citrus, peach, blackcurrant, tropical fruits, ginger, coffee, cinnamon, combinations (of the mentioned flavours) with mint flavours as well as spearmint and peppermint on their own). The combination inter alia of the flavours with further substances that have cooling, warming and/or mouth-watering properties is of particular interest.

Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest number of vitamins (e.g. B complex vitamins) act as precursors for enzyme cofactors, that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group—methyl, formyl, and methylene—in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols. Said vitamins may be present in the food composition in amounts of about 0.1 to about 5% b.w., and preferably about 0.5 to about 1% b.w.

Oral Composition

Another object of the present invention refers to an oral composition, comprising the sweetener composition or the extract as disclosed above. These compositions may further contain additional sweeteners or sweet-tasting compounds, aroma compounds, flavouring compounds and their mixtures as already described above.

Typical examples for non-food oral compositions encompass products for cleaning and protecting teeth and refreshing the oral cavity.

The oral compositions of the present invention typically comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. Nos. 4,518,615, 5,093,136, 5,266,336 5,601,858 or 6,986,709. In addition, chewing gum bases comprise further constituents, such as, for example, sugars, sugar substitutes or sweettasing substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations or products according to the invention (in particular those which are in the form of an oral care formulation or product or in the form of a formulation) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if said formulations or products comprise at least one or more aroma substances, chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alphapinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gammaoctalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, transrose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Pharmaceutical Compositions

Another object of the present invention refers to a pharmaceutical composition, comprising the sweetener composition or the extract as disclosed above. These compositions may further contain additional sweeteners or sweet-tasting compounds, aroma compounds, flavouring compounds and their mixtures as already described above.

Pharmaceutical compositions according to the present invention may include similar additives as already explained for the food and oral compositions, such as aroma and flavors. Pharmaceutical compositions may further include, oil bodies or emulsifiers and in particular co-actives supporting the beneficial properties of the pharmaceutical active agent. Therefore, the border between food compositions and pharmaceutical compositions is in flow and it should be understood that components cited for one application are recommended for the other mutatis-mutandis without literal repetition.

INDUSTRIAL APPLICATION

Another object of the present invention refers to a method for creating or enhancing a sweeting effect in a food or pharmaceutical composition encompassing adding an effective amount of the sweetening composition or the extract both cited above sufficient to produce the desired degree of sweetness to a composition that is intended for oral consumption. Usually, the sweetening composition or the extract are added to the food, the oral or the pharmaceutical composition in an amount of from 1 to about 2,000 ppm—calculated on the final composition.

Another object of the present invention refers to the use of the sweetening composition or the extract as described above as a sweetener for food or pharmaceutical compositions.

Preferably, one or more of the compound of formula (I) is used in an amount from 1 ppm to 2000 ppm by weight, based on the total weight of the composition and base on the total sum of all compounds of formula (I), if more than one compound of formula (I) is used. More preferably, the sweetener compounds of formula (I) are used in an amount from 10 ppm to 1000 ppm by weight, most preferably in an amount of 20 ppm to 500 ppm by weight, based on the total weight of the composition and base on the total sum of all compounds of formula (I), if more than one compound of formula (I) is used.

A final object of the present invention is related to a composition comprising
(i) at least one compound of formula (I), preferably compound A and/or B, and
(ii) at least one natural or artificial sweetener different from compounds of formula (I).

Blending artificial sweeteners, preferably selected from the group consisting of glucose, fructose, sucrose, sorbitol, mannitol, isomaltol, maltit, xylit, erythrit, stevia glycosides, in particular rebaudiosides A, D and M), stevia extracts, Acesulfam K, saccharin, aspartam, cyclamate, neohesperidin-dihydrochalcon, thaumatin, brazzein and mixtures thereof, with small amount of at least one compound of formula (I) leads to a synergistic increase in sweetening. Preferred compositions comprise the components (i) and (ii) in a ratio by weight of from 0.1 to 99.9 to about 5 to about 95% b.w.

EXAMPLES

The examples which follow are intended to illustrate the present invention without limiting the invention. Unless indicated otherwise all amounts, parts and percentages are based on the weight and the total amount or on the total weight and the total amount of the preparations.

Example 1

Extraction, Fractionation and Isolation of Stilbenes from *Gnetum formosum*

Extraction 545 g dried stems of *Gnetum formosum*, collected in Vietnam by Friedrich Nature Discovery, Euskirchen, Germany, were extracted with 6.8 L methanol-MTB-ether at room temperature for 24 h (yield: 43.7 g extract).

Pre-Fractionation by Reverse Phase Chromatography 43 g raw extract of *Gnetum formosum* were separated by reverse phase medium pressure chromatography under the following conditions:

stationary phase: RP-18, 40-63u (Merck)
mobile phase solvent A: water
mobile phase solvent B: methanol
gradient 72% solvent A to 24% solvent A in 60 min
column dimension: 50×250 mm Six Fractions were collected as set out in the following Table 1:

TABLE 1

| Fractions of C-1776 | | |
| --- | --- | --- |
| Fraction | Volume [ml] | Yield [g] |
| B-3554-A | 1500 | discarded |
| B-3554-B | 750 | 2,0850 |
| B-3554-C | 750 | 3,0225 |
| B-3554-D | 750 | 5,2576 |
| B-3554-E | 750 | 5,5349 |
| B-3554-F | 750 | 2,2874 |

Fraction B-3554-D contains Gnetifolin E (compound Aa) in >75% purity (HPLC with ELSD-detection).

Final Purification by Reverse Phase Chromatography

Fraction B-3554-F was separated by reverse phase chromatography to isolated pure stilbenes. The conditions for carrying out the separation are compiled in Table 2:

TABLE 2

| Conditions of the separation of B-3554-F | |
| --- | --- |
| stationary phase | LichrospherSelect B, 10 µm, 250 mm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 15-50% B in 57 min |
| detection | ELSD and UV |
| column dimension | 50 × 250 mm |
| used prefraction sample | 2.29 g B-3554-F |
| isolated compounds | B-3554-F-02: Gnetifolin E (compound Aa) |
| | B-3554-F-03: Rhapontigenin |
| | B-3554-F-01: Gnetifolin K |

Example 2

Extraction, Fractionation and Isolation of Stilbenes from *Bauhinia cardinalis*

Extraction 525 g dried leaves of *Bauhinia cardinalis*, collected in Vietnam by Friedrich Nature Discovery, Euskirchen, Germany, were extracted with 5.51 methanol-MTB-ether at room temperature for 24 h (yield: 69.9 g extract).

Pre-Fractionation by Reverse Phase Chromatography 69 g raw extract of *Bauhinia cardinalis* were separated by reverse phase medium pressure chromatography under the following conditions:

stationary phase: RP-18, 40-63u (Merck)
mobile phase solvent A: water
mobile phase solvent B: methanol
gradient 67% solvent A to 15% solvent A in 60 min
column dimension: 50×250 mm Six Fractions were collected as set out in the following Table 3:

TABLE 3

Fractions of H-0956

| Fraction | Volume [ml] | Yield [g] |
|---|---|---|
| H-0956-A | 1500 | discarded |
| H-0956-B | 750 | discarded |
| H-0956-C | 750 | 2,0175 |
| H-0956-D | 750 | 6,6300 |
| H-0956-E | 750 | 7,6349 |
| H-0956-F | 750 | 3,5251 |
| H-0956-G | 750 | 1,3875 |

Final Purification by Reverse Phase Chromatography

Fraction H-0956-C was separated by reverse phase chromatography to isolated pure stilbenes. The conditions for carrying out the separation are compiled in Table 4:

TABLE 4

Conditions of the separation of H-0956-C

| | |
|---|---|
| stationary phase | LichrospherSelect B, 10 μm, 250 mm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 18-43% B in 57 min |
| detection | ELSD and UV |
| column dimension | 50 × 250 mm |
| used prefraction sample | 6.63 g H-0956-C |
| isolated compounds | H-0956-C-04: Piceatannolglucosid |

Example 3

Analytical Characterization of Isolated Stilbenes

Fractions from preparative HPLC were collected (40 ml each) and analyzed by HPLC-MS. Fractions containing the same compound according to retention time and mass spectrum were combined, evaporated and analyzed by HPLC-MS and NMR ($^1$H-NMR. HH-COSY. HSQC. HMBC). Structures were elucidated by interpretation of NMR and MS data. The conditions for carrying out HPLC-MS are compiled in Table 5:

TABLE 5

Conditions of the HPLC-MS of isolated compounds

| | |
|---|---|
| HPLC | HPLC PE series 200 |
| MS System | Applied Biosystems API 150 or API 165 |
| datasystem | Analyst 1.3 |
| stationary phase | Phenomenex Luna C8 (2). 5 μm. 50 × 4.6 mm |
| flowrate | 1.2 mL/min |
| detection | (+/(−)-ESI. Fast-Switching-Mode. ELSD (Sedex 75) |
| injection volume | 10 μL |
| mobile phase: | A: 5 mM Ammoniumformiat and 0.1% formic acid |
| | B: Acetonitril/Methanol = 1:1 + 5 mM Ammoniumformiat + 0.1% formic acid (pH 3) |

| | time [min] | % A | % B |
|---|---|---|---|
| gradient | 0 | 95 | 5 |
| | 6 | 0 | 100 |
| | 8 | 0 | 100 |

Compound Aa

Gnetifolin E

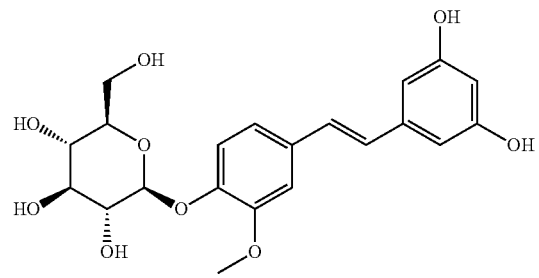 [SMILES: COc1cc(/C=C/c2cc(O)cc(O)c2)ccc1O[C@@H]1O[C@H](CO)[C@@H](O)[C@H](O)[C@H]1O]

Compound Bb

Piceatannol 4'-O-β-D-glucopyranoside

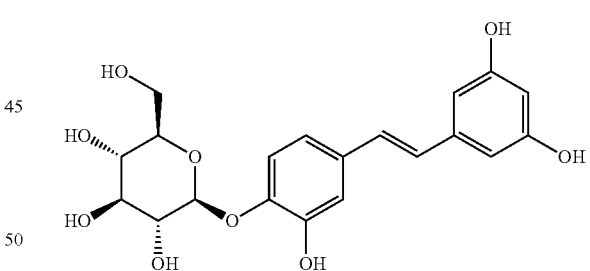

Example 4

Organoleptic Test of the Compounds of Formula (I) Against Sucrose

Intrinsic sweet taste: The isolated pure compounds were dissolved in non-carbonated mineral water ("Fonsana Quelle") in a concentration of 0.5 mg/ml (500 ppm). The sweet taste of each sample was compared by a panel of 4 panelists with a solution of sucrose in a concentration of 20 mg/ml. The sweetness of the compounds Aa and Bb is comparable with the control solution. Both compounds showed no significant off-taste.

Example 5

Organoleptic Test of the Compounds of Formula (I) in Combination with Known Sweeteners Combination of (I) with Sucrose.

The sweetness enhancement properties of compound Aa and Bb was determined using a sample having a concentration of 100 μg/ml compound Aa and Bb, which is near the sweetness detection threshold, in 7% sucrose solution. The compound Aa and Bb sample was directly compared to samples of 7%, 8% or 9% sucrose, and panelists were instructed to compare the sweetness intensity of the samples. The comparisons were carried out by a panel of 3 sweet sensitive panelists. All samples were presented to panelists in 5 ml aliquots at ambient temperature. Panelists compared the compound Aa and Bb sample to each of the sucrose samples.

Both tested compounds dissolved in 7% sucrose showed a sweetness of at least equal to 9% sucrose.

Example 6

Formulation Examples

The following Tables 6a to 6f provide some examples for oral compositions comprising at least one of the sweeteners disclosed before.

TABLE 6a

Chewing gum, free of sugar; all amounts in % b.w.

| Composition | I | II | III |
|---|---|---|---|
| Gum base | 30.00 | 30.00 | 30.00 |
| Sorbit, powdered | 40.00 | 40.00 | 40.00 |
| Isomalt, powdered | 9.50 | 9.50 | 9.50 |
| Xylitol | 2.00 | 2.00 | 2.00 |
| Mannit D | 3.00 | 3.00 | 3.00 |
| Compound Aa | 0.05 | — | 0.025 |
| Compound Bb | — | 0.1 | 0.025 |
| Emulgum/Plasticizing agent | 0.30 | 0.30 | 0.30 |
| Sorbitol (70% water) | 13.00 | 13.00 | 13.00 |
| Spearmint aroma | 1.00 | 1.00 | 1.00 |
| Glycerol | | Ad 100 | |

TABLE 6b

Tooth paste; all amounts in % b.w.

| Composition | IV | V | VI |
|---|---|---|---|
| Glycerol | 20.00 | 20.00 | 20.00 |
| Solbrol M (sodium salt) | 0.15 | 0.15 | 0.15 |
| Sodium monofluor phosphate | 0.76 | 0.76 | 0.76 |
| Compound Aa | 0.10 | — | 0.05 |
| Compound Bb | — | 0.1 | 0.05 |
| Dicalciumphosphate dihydrate | 36.00 | 36.00 | 36.00 |
| Aerosil 200 | 3.00 | 3.00 | 3.00 |
| Sodium carboxymethyl cellulose | 1.20 | 1.20 | 1.20 |
| Sodium lauryl sulfate | 1.30 | 1.30 | 1.30 |
| Peppermint aroma | 1.00 | 1.00 | 1.00 |
| Deionised water | | Ad 100 | |

TABLE 6c

Mouth wash concentrate; all amounts in % b.w.

| Composition | VII | VIII | IX |
|---|---|---|---|
| Ethanol 96% | 42.00 | 42.00 | 42.00 |
| Cremophor RH 455 | 5.00 | 5.00 | 5.00 |
| Allantoin | 0.20 | 0.20 | 0.20 |
| Compound Aa | 0.1 | — | 0.05 |
| Compound Bb | — | 0.1 | 0.05 |
| Colour L-Blue 5000 (1% in Wasser) | 0.03 | 0.03 | 0.03 |
| Spearmint aroma | 2.00 | 2.00 | 2.00 |
| Deionised water | | Ad 100 | |

TABLE 6d

Hard boiled candy, sugar-free; all amounts in % b.w.

| Composition | X | XI | XII |
|---|---|---|---|
| Isomalt | 94.98 | 94.98 | 94.98 |
| Xylitol | 2.40 | 2.40 | 2.40 |
| Compound Aa | 0.1 | — | 0.05 |
| Compound Bb | — | 0.1 | 0.05 |
| Citric acid | 0.050 | 0.050 | 0.050 |
| Cherry aroma | 0.25 | 0.25 | 0.25 |
| Water | | Ad 100 | |

TABLE 6e

Ice tea

| Composition | XIII | XIV | XV |
|---|---|---|---|
| Sucrose | 3.75 | 3.75 | 1.25 |
| Black Tea Powder | 0.25 | 0.25 | 0.25 |
| Citric Acid | 0.09 | 0.09 | 0.09 |
| Potassium Sorbate | 0.015 | 0.015 | 0.015 |
| Peach Flavour | 0.03 | 0.03 | 0.03 |
| Compound Aa | — | 0.04 | 0.02 |
| Compound Bb | 0.05 | 0.04 | — |
| Rebaudioside A | — | — | 0.01 |
| Water | | Ad 100 | |

TABLE 6f

Carbonated soft drink

| Composition | XVI | XVII | XVIII |
|---|---|---|---|
| Sucrose | 3.0 | 3.0 | 1.0 |
| Cola Flavour | 0.4 | 0.4 | 0.4 |
| Phosphoric acid 85% | 0.03 | 0.03 | 0.03 |
| Caffeine | 0.01 | 0.01 | 0.01 |
| Compound Aa | 0.05 | 0.02 | |
| Compound Bb | | 0.02 | 0.02 |
| Acesulfam K | | | 0.01 |
| Carbonated water | | Ad 100 | |

The invention is further illustrated by analytical data provided in the following FIGS. 1 to 4:

FIG. 1: H-NMR of compound A
FIG. 2: H-NMR of compound B
FIG. 3: ESI-MS of compound A
FIG. 4: ESI-MS of compound B

The invention claimed is:
1. A sweetener composition comprising:
(a) a component comprising an effective amount of a compound selected from the group consisting of Gnetifolin E and Piceatannol-4'-O-β-D-glucoside and mixtures thereof; and

(b) a separate component selected from the group consisting of: sucrose, glucose, fructose, rebaudioside A, rebaudioside D, rebaudioside M, and mixtures thereof; and wherein said effective amount of said compound potentiates sweetness of said separate component (b).

2. A food composition, comprising the sweetener composition of claim 1.

3. The food composition of claim 2, in the form of a soft drink, a dairy product, a cereal product or a confection.

4. An oral composition, comprising a composition comprising
- (a) a compound selected from the group consisting of Gnetifolin E, Piceatannol-4'-O-ß-D-glucoside, and mixtures thereof, and
- (b) a separate component selected from the group consisting of sucrose, glucose, fructose, rebaudioside A, rebaudioside D, rebaudioside M, and mixtures thereof, said compound (a) present in an amount to potentiate sweetness of said separate component (b).

5. A pharmaceutical composition, comprising the sweetener composition of claim 1.

6. A method for creating or enhancing a sweetening effect in a food or pharmaceutical composition comprising adding an effective amount of the sweetener composition of claim 1 sufficient to produce the desired degree of sweetness to a composition that is intended for oral consumption.

7. A food composition in the form of an orally consumable or ready-to-eat foodstuff or a frozen product, comprising the sweetener composition of claim 1.

8. The food composition of claim 7, in the form of a soft drink, a dairy product, a cereal product or a confection.

9. The sweetener corn position of claim 1, wherein the component (a) is an extract obtained by aqueous and/or alcoholic extraction of at least one plant selected from the group consisting of: *Gnetum formosum, Gnetum montanum, Picea abies, Picea glauca, Rheum officinale, Rheum palmatum, Rheum rhaponticum, Rheum emodi, Rheum rhbarbarum, Eucalyptus globulus, Eucalyptus camaldudensis, Bauhinia cardinalis, Polygonum sacchalinense, Polygonum japonicum*, and mixtures thereof.

10. A food composition, comprising the composition of claim 9.

11. The composition of claim 10, further comprising a component selected from the group consisting of additional sweeteners or sweet-tasting compounds, aroma compounds, flavouring compounds and mixtures thereof.

12. An oral composition, comprising the composition of claim 9.

13. A pharmaceutical composition, comprising the composition of claim 9.

14. A method for creating or enhancing a sweetening effect in a food or pharmaceutical composition comprising adding an effective amount of the composition of claim 9 sufficient to produce the desired degree of sweetness to a composition that is intended for oral consumption.

* * * * *